US011547707B2

(12) United States Patent
Román et al.

(10) Patent No.: US 11,547,707 B2
(45) Date of Patent: Jan. 10, 2023

(54) CARBAMOYL CYCLOHEXANE DERIVATIVES FOR TREATING AUTISM SPECTRUM DISORDER

(71) Applicant: Richter Gedeon Nyrt., Budapest (HU)

(72) Inventors: Viktor Román, Érd (HU); Nika Adham-Parangi, Englewood, NJ (US); Willie Roger Earley, West Chester, PA (US); Paul Po-Jen Yeung, Southeastern, PA (US)

(73) Assignee: Richter Gedeon Nyrt., Budapest (HU)

( * ) Notice: Subject to any disclaimer, the term of this patent is extended or adjusted under 35 U.S.C. 154(b) by 104 days.

(21) Appl. No.: 16/845,192

(22) Filed: Apr. 10, 2020

(65) Prior Publication Data
US 2020/0323842 A1    Oct. 15, 2020

Related U.S. Application Data

(60) Provisional application No. 62/831,981, filed on Apr. 10, 2019.

(51) Int. Cl.
*A61K 31/495* (2006.01)
*A61P 25/00* (2006.01)
*A61K 31/5377* (2006.01)

(52) U.S. Cl.
CPC ........ *A61K 31/495* (2013.01); *A61K 31/5377* (2013.01); *A61P 25/00* (2018.01)

(58) Field of Classification Search
CPC .... A61K 31/495; A61K 31/5377; A61P 25/00
See application file for complete search history.

(56) References Cited

U.S. PATENT DOCUMENTS

| | | |
|---|---|---|
| 4,666,911 A | 5/1987 | Fujimura et al. |
| 4,943,632 A | 7/1990 | Robinson |
| 4,957,921 A | 9/1990 | Caprathe et al. |
| 5,384,323 A | 1/1995 | Bolz |
| 5,807,575 A | 9/1998 | Dumoulin |
| 5,846,514 A | 12/1998 | Foster et al. |
| 5,910,319 A | 6/1999 | Anderson et al. |
| 6,334,997 B1 | 1/2002 | Foster et al. |
| 6,395,739 B1 | 5/2002 | Sato et al. |
| 6,489,341 B1 | 12/2002 | Jerussi |
| 6,528,529 B1 | 3/2003 | Brann et al. |
| 6,566,550 B2 | 5/2003 | Lowe, III |
| 6,667,060 B1 | 12/2003 | Vandecruys |
| 6,919,342 B2 | 7/2005 | Haupt |
| 7,122,576 B2 | 10/2006 | Plata-Salaman et al. |
| 7,737,142 B2 | 6/2010 | Csongor et al. |
| 7,829,569 B2 | 11/2010 | Liao et al. |
| 7,875,610 B2 | 1/2011 | Szalai et al. |
| 7,943,621 B2 | 5/2011 | Czibula et al. |
| 7,981,897 B2 | 7/2011 | Bathe et al. |
| 8,569,496 B2 | 10/2013 | Czibula et al. |
| 8,569,497 B2 | 10/2013 | Czibula et al. |
| 8,569,498 B2 | 10/2013 | Czibula et al. |
| 8,765,765 B2 | 7/2014 | Csongor et al. |
| 8,802,672 B2 | 8/2014 | Szalai et al. |
| 8,802,888 B2 | 8/2014 | Mathe et al. |
| 8,846,100 B2 | 9/2014 | Shojaei |
| 9,056,845 B2 | 2/2015 | Sarkar et al. |
| 9,056,846 B2 | 2/2015 | Sarkar et al. |
| RE47,333 E | 4/2019 | Sarkar et al. |
| RE47,350 E | 4/2019 | Sarkar et al. |
| RE49,110 E | 6/2022 | Sarkar et al. |
| 2001/0009912 A1 | 7/2001 | Tsaklakidis et al. |
| 2003/0144285 A1 | 7/2003 | Brann et al. |
| 2004/0259882 A1 | 12/2004 | Haupt et al. |
| 2005/0107397 A1 | 5/2005 | Galambos et al. |
| 2006/0229297 A1 | 10/2006 | Csongor et al. |
| 2007/0099931 A1 | 5/2007 | Ghosh et al. |
| 2007/0244093 A1 | 10/2007 | Boehm et al. |
| 2007/0259885 A1 | 11/2007 | Bathe et al. |
| 2009/0023750 A1 | 1/2009 | Czibula et al. |

(Continued)

FOREIGN PATENT DOCUMENTS

| | | |
|---|---|---|
| CN | 105218484 | 1/2016 |
| CN | 105330616 | 2/2016 |

(Continued)

OTHER PUBLICATIONS

Lord et al., Lancet, vol. 392, publ. Aug. 2, 2018, pp. 508-520 (Year: 2018).*
S. H. Kim, et al., "Preparation method of 4-biphenylacetic acid with high yield and high purity," Database WPI Week 200648, Thomson Scientific, London AN 206-468774, XP0-02581633, May 5, 2011.
"The ICD-10 classification of mental and behavioral disorders : clinical descriptions and diagnostic guidelines," Geneva; World Health Organization, 1992, 263 pages.
Abraham, Ed., "History of Quantitative Structure-Activity Relationships," Burger's Medicinal Chemistry and Drug Discovery, 6th edition, vol. 1, pp. 1-48, (Jan. 2003).
Abstracts of Papers, 234th ACS National Meeting, Boston, MA, United States, Aug. 19-23, 2007, MEOI-383, Jul. 25, 2007, 268 pages.
Aiken, "Pramipexole in psychiatry: A systematic review of the literature," *J. Clin Psychiatry.*, 68(8):1230-1236, (2007).
Alphs et al, "Asenapine in the Treatment of Negative Symptoms of Schizophrenia: Clinical Trial Design and Rationale Psychopharmacology Bulletin," 2007, 40(2):41-53.

(Continued)

*Primary Examiner* — Sarah Pihonak
(74) *Attorney, Agent, or Firm* — Fish & Richardson P.C.

(57) ABSTRACT

The present invention relates to trans-N-[4-[2-[4-(2,3-dichlorophenyl)piperazin-1-yl]ethyl]cyclohexyl]-N',N'-dimethylurea (cariprazine), its salts, close analogs, derivatives, pharmaceutical compositions, metabolites and combinations for use in the treatment of symptoms of autism spectrum disorder in general, and preferably the object of the present invention is to treat one or more symptoms of autism.
Furthermore, it was also found that cariprazine, its salts, close analogs, derivatives, pharmaceutical compositions, metabolites and combinations are suitable for treatment of conditions such as Asperger's syndrome, atypical autism (otherwise known as pervasive developmental disorder not otherwise specified; PDD-NOS), Rett syndrome, childhood disintegrative disorder, attention deficit hyperactivity disorder (ADHD) and sensory integration dysfunction.

15 Claims, 6 Drawing Sheets

(56) References Cited

U.S. PATENT DOCUMENTS

| | | | |
|---|---|---|---|
| 2009/0036468 | A1 | 2/2009 | Samoriski et al. |
| 2009/0275597 | A1* | 11/2009 | Papadakis .............. A61K 31/13 514/579 |
| 2010/0016334 | A1 | 1/2010 | Sarkar |
| 2010/0137335 | A1 | 6/2010 | Csongor et al. |
| 2010/0197666 | A1 | 8/2010 | Laszlovsky et al. |
| 2010/0197704 | A1 | 8/2010 | Laszlovsky et al. |
| 2010/0256145 | A1 | 10/2010 | Bak-Jensen et al. |
| 2011/0059980 | A1 | 3/2011 | Oobayashi |
| 2011/0269959 | A1 | 11/2011 | Csongor et al. |
| 2011/0275804 | A1 | 11/2011 | Czibula et al. |
| 2011/0275816 | A1 | 11/2011 | Czibula et al. |
| 2011/0288329 | A1 | 11/2011 | Mathe et al. |
| 2013/0040966 | A1 | 2/2013 | Sarkar |
| 2013/0224172 | A1* | 8/2013 | Fallon .................. A61P 1/12 424/94.63 |
| 2015/0306094 | A1 | 10/2015 | Pitter |
| 2019/0117647 | A1 | 4/2019 | Imada et al. |
| 2020/0222391 | A1 | 7/2020 | Konta et al. |
| 2021/0276965 | A1 | 9/2021 | Neu et al. |

FOREIGN PATENT DOCUMENTS

| | | |
|---|---|---|
| EP | 0224751 | 10/1987 |
| EP | 0453574 | 10/1991 |
| EP | 0431580 | 3/1995 |
| EP | 2251011 | 11/2010 |
| EP | 16165247 | 10/2017 |
| JP | 01-199977 | 8/1989 |
| JP | 01-308284 | 12/1989 |
| JP | 04-275280 | 9/1992 |
| JP | 05-032586 | 2/1993 |
| JP | 05-310745 | 11/1993 |
| KR | 20050043131 | 5/2005 |
| KR | 10-2006-0058096 | 5/2006 |
| WO | WO 1991/07411 | 5/1991 |
| WO | WO 1997/011070 | 3/1997 |
| WO | WO 1999/050247 | 10/1999 |
| WO | WO 1999/067206 | 12/1999 |
| WO | WO 2001/005763 | 1/2001 |
| WO | WO 2003/029233 | 4/2003 |
| WO | WO 2003/064393 | 8/2003 |
| WO | WO 2005/012266 | 2/2005 |
| WO | WO 2006/034774 | 4/2006 |
| WO | WO 2006/044524 | 4/2006 |
| WO | WO 2006/082456 | 8/2006 |
| WO | WO 2007/033191 | 3/2007 |
| WO | WO 2008/038003 | 4/2008 |
| WO | WO 2008/139235 | 11/2008 |
| WO | WO 2008/141135 | 11/2008 |
| WO | WO 2008/142461 | 11/2008 |
| WO | WO 2008/142462 | 11/2008 |
| WO | WO 2009/020897 | 2/2009 |
| WO | WO 2009/104739 | 8/2009 |
| WO | WO 2010/009309 | 1/2010 |
| WO | WO 2010/070368 | 6/2010 |
| WO | WO 2010/070369 | 6/2010 |
| WO | WO 2010/126527 | 11/2010 |
| WO | WO 2011/060363 | 5/2011 |
| WO | WO 2013/169101 | 11/2013 |
| WO | WO 2014/031162 | 2/2014 |
| WO | WO 2014/083522 | 6/2014 |
| WO | WO 2015/056164 | 4/2015 |
| WO | WO 2015/086836 | 6/2015 |

OTHER PUBLICATIONS

Archer and Kostrzewa, "Neuroteratology and Animal Modeling of Brain Disorders," Neurotoxin Modeling of Brain Disorders—Lifelong Outcomes in Behavioral Teratology, 2015, pp. 1-40.

Artursson et al., "Correlation between oral drug absorption in humans and apparent drug permeability coefficients in human intestinal epithelial (Caco-2) cells," Biochem. Biophys. Res. Comm., 1991, 175(3):880-885.

Auclair et al., "P.3.c. Psychotic disorders and treatment—Treatment (basic)" World Congress of The International College of Neuropsychopharmacology, 2014, 1 page.

Baldessarini and Tarazi, "Pharmacotherapy of Psychosis and Mania," Brunton et al. (eds.), Goodman and Gilman's The Pharmacological Basis of Therapeutics, 11th Edition, McGraw Hill, Chapter 18, pp. 461-500, (2005).

Bambini-Junior et al., "Animal model of autism induced by prenatal exposure to valproate: behavioral changes and liver parameters," Brain Res., Aug. 2011, 1408:8-16.

Barnes et al., "Evidence-based guidelines for the pharmacological treatment of schizophrenia: recommendations from the British Association for Psychopharmacology," J Psychopharmacol., 25(5):567-620, (Epub Feb. 3, 2011).

Belliotti et al., "Novel Cyclohexyl Amides as Potent and Selective 0 3 Dopamine Receptor Liqands," Bioorq. Med. Chem. Lett., 1997, 7(18):2403-2408.

Berge et al., "Pharmaceutical salts," *Journal of Pharmaceutical Sciences*, 66(1):1-19 (1977).

Bézard et al., "Attenuation of levodopa-induced dyskinesia by normalizing dopamine D3 receptor function," *Nat. Med.*, 9(6):762-767, (2003).

Brugha et al., "Epidemiology of autism spectrum disorders in adults in the community in England," Arch. Gen. Psychiatry, May 2011, 68(5):459-65.

Buchanan et al, "Asenapine Versus Olanzapine in People With Persistent Negative Symptoms of Schizophrenia," Journal of Clinical Psychopharmacology, Feb. 2012, 32:1:36-45.

Carpenter et al., "Treatment of negative symptoms," *Schizophr Bull.*, 11(3):440-452, 1985.

CDC "Prevalence of Autism Spectrum Disorder Among Children Aged 8 Years—Autism and Developmental Disabilities Monitoring Network," Morbidity and Mortality Weekly Report Surveillance Summaries, 2018, 67(6):1-23.

Chadman, "Fluoxetine but not risperidone increases sociability in the BTBR mouse model of autism," Pharmacol. Biochem. Behav., Jan. 2011, 97(3):586-94.

Chen et al., "A New and Practical Synthesis of Cariprazine through the Facile Construction of 2-[trans-4-(3,3 Dimethylureido)cyclohexyl] acetic Acid," Synthesis, Jun. 2016, 48(18):A-G.

Christensen et al., "Prenatal valproate exposure and risk of autism spectrum disorders and childhood autism," Jama, Apr. 2013, 309(16): 1696-703.

ClinicalTrials.gov, NCT02165098, "Cariprazine: Comparison of Slow- and Immediate-Release Forms," dated Mar. 24, 2016, 6 pages.

Creese et al., "Species variation in dopamine receptor binding," Eur. J. Pharmacol., 60:55-66, (1979).

Damasio, "Alzheimer's Disease and Related Dementias," Cecil Textbook of Medicine, 20th Edition, vol. 2, pp. 1992-1996, (1996).

de Berardis, et al., "The novel antipsychotic cariprazine (RGH-188): state-of-the-art in the treatment of psychiatric disorders," Current Pharmaceutical Design, 2016, 22(33):5044-5162.

Dean, [Editor]. "Recent Advances in the Synthesis and Applications of Radiolabeled Compounds for Drug Discovery and Development," Curr., Pharm. Des., vol. 6, No. 10, [Table of Contents] CAN 133:68895 AN 2000:473538 CAPLUS; 3 pages, (2000).

Deshpande et al., "Design and evaluation of oral bioadhesive controlled release formulations of miglitol, intended for prolonged inhibition of intestinal α-glucosidases and enhancement of plasma glucagon like peptide-1 levels," International Journal of Pharmaceutics, 2009, 380(1-2)16-24.

Di Chiara, "Drug addiction as dopamine-dependent associative learning disorder," Eur. J. Pharmacol., 375: 13-30, (1999).

Eli Lilly and Company, "Zyprexa Olanzapine Tablets . . . " MedWatch Safety Alerts for Human Medical Products, FDA [online]. Retrieved from the Internet: URL: http://www.fda.gov/medwatch/safety/2006/Aug_PIs/Zyprexa_PI.pdf>, 31 pages, (2004).

Elsabbagh et al., "Global prevalence of autism and other pervasive developmental disorders," Autism research, Jun. 2012, 5(3): 160-179.

(56) References Cited

OTHER PUBLICATIONS

EP Search Report in European Appln. No., PCT/HU2009/000107, dated May 27, 2010, dated May 27, 2010, 3 pages.

Evans, "Synthesis of radiolabeled compounds," J. Radioanal. Chem., 64(1-2):9-32, (1981).

FDA guidelines, "Dissolution Testing of Immediate Release Solid Oral Dosage Forms," dated Aug. 1997, Section IV-A, 5 pages.

FDA guidelines, "Extended Release Oral Dosage Forms: Development, Evaluation and Application of In Vitro/In Vivo Correlation", Food and Drug Administration, CDER, Sep. 1997, p. 17.

FDA guidelines, "Q3B(R2) Impurities in New Drug Products," Revision 2, Jul. 2006, 18 pages.

Gandal et al., "Validating γ oscillations and delayed auditory responses as translational biomarkers of autism," Biological psychiatry, Dec. 2010, 68(12): 1100-1106.

Glase et al., "4-bromo-l-methoxy-N-[2-(4-aryl-l-piperazinyl)ethyl]-2-naphthalenecarboxamides: Selective dopamine D3 receptor partial agonists," Bioorganic & Medicinal Chemistry Letters, 6(12):1361-1366, (1996).

Goodwin et al., "Medical Treatment of Acute Bipolar Depression," Manic-Depressive Illness, New York: Oxford University Press, pp. 639-651, (1990).

Grabovac et al., "Comparison of the mucoadhesive properties of various polymers," Advanced Drug Delivery Reviews, 2005, 57(11):1713-1723.

Graff-Guerrero et al., "The effect of antipsychotics on the high-affinity state of D2 and D3 receptors: a positron emission tomography study With [11C]-(+)-PHNO," Arch. Gen. Psychiatry, Jun. 2009, 66(6):606-615.

Greengrass et al., "Binding characteristics of 3H-prazosin to rat brain alpha-adrenergic receptors," Eur. J. Pharmacol., 55(3):323-326, (1979).

Grunder et al., "Brain and plasma pharmacokinetics of aripiprazole in patients with schizophrenia: an [18F] fallypride PET study," Am. J. Psychiatry, Aug. 2008, 165(8):988-995.

Guérémy et al., "2-Amino-6-chloro-4-(N-methylpiperazino)pyrimidines, inhibitors of spiroperidol binding," J. Med. Chem., 1982, 25(12):1459-1465.

Gurevich et al., "Mesolimbic dopamine D3 receptors and use of antipsychotics in patients with schizophrenia. A postmortem study." Arch Gen Psychiatiy., 54(3):225-232, (1997).

Gurevich et al., "Distribution of dopamine D3 receptor expressing neurons in the human forebrain: comparison with D2 receptor expressing neurons," Neuropsychopharmacology, 20(1):60-80, (Jan. 1999).

Guy et al., ECDEU Assessment Manual for Psychopharmacology. Rockville, Md: US Department of Health, Education, and Welfare, pp. 218-222, Publication ADM 76-338, (1976).

Gyertyan et al., Effects of RGH-237 [N-{4-[4-(3-Aminocarbonyl-phenyl)-piperazin-l-yl]-butyl}-4-bromo-benzamide], an Orally Active, Selective Dopamine D3 Receptor Partial Agonist in Animal Models of Cocaine Abuse, Journal of Pharmacology and Experimental Therapeutics., Mar. 2007, 320(3):1268-78.

Gyertyan et al., "RGH-790, A selective dopamine D3/D2 receptor partial agonist with cognitive enhancer properties," World Psychiatric Association International Conference, Prague, 1 page [poster], (Oct. 17-21, 2012).

Gyertyán et al., "Subnanomolar dopamine D3 receptor antagonism coupled to moderate D2 affinity results in favourable antipsychotic-like activity: Behavioral Data," Int. J. Neuropsychopharmacol., 5 Suppl. 1:S174, Abstract No. P.3.W.071, (2002).

Gyertyan et al., "Effects of dopamine $D_3$ receptor antagonists on spontaneous and agonist-reduced motor activity in NMRI mice and Wistar rats: comparative study with nafadotride, U 99194A and SB 277011," Behavioural Pharmacology, 15(4):253-262, (2004).

Gyertyán et al., "The selective dopamine D3 receptor antagonists, SB 277011-A and S 33084 block haloperidol-induced catalepsy in rats," Eur. J. Pharmacol., 572:171-174, (2007).

Han et al., "Advances in Characterization of Pharmaceutical Hydrates," Trends in Bio/Pharmaceutical Industry, 2006, 2(3):25-29.

Hara et al., "Risperidone and aripiprazole alleviate prenatal valproic acid-induced abnormalities in behaviors and dendritic spine density in mice," Psychopharmacology (Berl), Nov. 2017, 234(21):3217-3228.

Heidbreder et al., "The role of central dopamine D3 receptors in drug addiction: a review of pharmacological evidence," Brain Res. Rev., 49:77-105, (2005).

Heusler et al., "In vitro profile of the new antipsychotic, F17464, at recombinant human neurotransmitter receptors," Eur. Neuropsychopharm. 2016, 26(S2):S490-S491.

Ichikawa et al., "Aripiprazole in the Treatment of Irritability in Children and Adolescents with Autism Spectrum Disorder in Japan: A Randomized, Double-blind, Placebo-controlled Study," Child Psychiatry Hum, Dev., Oct. 2017, 48(5):796-806.

Janssen, "Risperdal Consta (risperidone) Long-Acting Injection," MedWatch Safety Alerts for Human Medical Products, FDA [online] Retrieved from the Internet:<URL: http://www.fda.gov/medwatch/safety/2006/Sep_PIs/RisperdalConsta_PI.pdf>, 39 pages (2006).

Joyce, "Dopamine D3 receptor as a therapeutic target for antipsychotic and antiparkinsonian drugs," Pharmacol Ther., 90:231-259, (2001).

Kabalka and Varma, "The synthesis of radiolabeled compounds via organometallic intermediates," Tetrahedron, 45(21):6601-6621, (1989).

Kay et al., "The positive and negative syndrome scale (PANSS) for schizophrenia," Schizophr. Bull., 13:261-276, (1987).

Keck, "The management of acute mania," British Medical Journal, 327(7422):1002-1003, (2003).

Keith, "Advances in psychotropic formulations," Prog Neuro-Psychopharmacol Biol Psychiatry., Aug. 30, 2006, 30(6):996-1008.

Kelley et al., "Empirical validation of primary negative symptoms: independence from effects of medication and psychosis," Am J Psychiatry., 156:406-411, 1996.

King and Schwartz, "Oral solid dosage forms," Remington's Pharmaceutical Sciences, Gennaro, A., Ed., 17th Edition, Mack Publishing Company, Easton PA, Chapter 90, pp. 1603-1632, (1985).

Kiss et al., "Cariprazine (RGH-188), a dopamine D(3) receptor-preferring, D(3)/D(2) dopamine receptor antagonist-partial agonist antipsychotic candidate: in vitro and neurochemical profile," J. Pharmacol. Exp. Ther., Apr. 2010, 333(1):328-40.

Krause et al., "Antipsychotic drugs for patients with schizophrenia and predominant or prominent negative symptoms: a systematic review and metaanalysis," European Archives of Psychiatry and Clinical Neuroscience, Oct. 2018, 268(7):625-639.

Laszlovsky et al., "Dopamine 02/03 Receptor Occupancy of RGH-188, a 03/02 Antagonist/Partial Agonist Antipsychotic, in Healthy Volunteers," 20th Congress of the European College of Neuropsychopharmacology, Vienna Austria, Oct. 13-17, 2007 , 1 page.

Laszy et al., "Dopamine D3 receptor antagonists improve the learning performance in memory impaired rats," Psychopharmacol., 179(3):567-575, (2005).

Layzer, "Degenerative Diseases of the Nervous System," Cecil Textbook of Medicine, 20th Edition, vol. 2, pp. 2050-2057, (1996).

Le Foll et al., "Dopamine D3 receptor ligands for the treatment of tobacco dependence," Expert Opin Investig Drugs, 16(1)45-57, (2007).

LeClerc et al., "Pharmacological therapies for autism spectrum disorder: a review," P. T., Jun. 2015, 40(6):389-397.

Lehman et al., "Practice guideline for the treatment of patients with schizophrenia, second edition," Am. J. Psychiatry, 161(2 Suppl):1-56, (2004).

Lehr et al., "Lectin-mediated drug delivery: The second generation of bioadhesives," Journal of Controlled Release, 2000, 65(1-2):19-29.

Lenert et al., "Public preferences for health states with schizophrenia and a mapping function to estimate utilities from positive and negative symptom scale scores," Schizophr Res., 71(1):155-165, (Nov. 1, 2004).

Leucht et al., "Second-generation versus first-gerneration antipsychotic drugs for schizophrenia: a meta-analysis," Lancet, 2009, 373:31-41.

Levant and McCarson, "D(3) dopamine receptors in rat spinal cord: implications for sensory and motor function," Neurosci Lett., 303(1):9-12, (Apr. 2001).

(56) References Cited

OTHER PUBLICATIONS

Levant et al., "Dopamine $D_3$ receptor: relevance for the drug treatment of Parkinson's disease," CNS Drugs, 12:391-402, (1999).
Levant, "The D3 dopamine receptor: neurobiology and potential clinical relevance," Pharmacol. Rev., 49(3):231-252, (1997).
Lim et al., "Pharmacological rescue of Ras signaling, GluAl-dependent synaptic plasticity, and learning deficits in a fragile X model," Genes Dev., Feb. 2014, 28(3):273-289.
Ludwig et al., "The use of mucoadhesive polymers in ocular drug delivery," Advanced Drug Delivery Reviews, 2005, 57(11):1595-1639.
Mailman et al., "Third generation antipsychotic drugs: partial agonism or receptor functional selectivity?" Curr Pharm Des., 2010, 16(5)488-501.
Maj et al., "Effect of antidepressant drugs administered repeatedly on the dopamine D3 receptors in the rat brain," Eur. J. Pharmacol. 351:31-37, (1998).
Martineau et al., "Catecholaminergic metabolism and autism," Dev. Med. Child. Neurol., Aug. 1994, 36(8):688-697.
McBride et al., "Serotonergic Responsivity in Male Young Adults With Autistic Disorder," Results of a pilot study: Arch. Gen. Psychiatry., Mar. 1989, 46(3):213-21.
Millan et al., "S33084, a novel, potent, selective, and competitive antagonist at dopamine D(3)-receptors: II. Functional and behavioral profile compared with GR218,231 and L741,626," J. Pharmacol. Exp. Ther., 293:1063-1073, (2000).
Millan et al., "The dopamine D3 receptor antagonist, (+)-S 14297, blocks the cataleptic properties of haloperidol in rats," Eur. J. Pharmacol., 321:R7-R9, (1997).
Montgomery and Asberg, "A new depression scale designed to be sensitive to change," Br. J. Psychiatry, 134:382-389, (1979).
Morissette et al., "High-throughput crystallization: polymorphs, salts, co-crystals and solvates of pharmaceutical solids," Adv Drug Deliv Rev. 56(3):275-300, Feb. 2004.
Mueser and McGurk, "Schizophrenia," Lancet, 363:2063-2072, (2004).
Müller-Oerlinghausen et al., "Bipolar disorder," Lancet, 359(9302):241-247, (2002).
Muly et al., "Relationship between dose, drug levels, and D2 receptor occupancy for the atypical antipsychotics risperidone and paliperidone," J Pharmacol Exp Ther, Apr. 2012, 341(1):81-9.
Murphy et al., "Autism spectrum disorder in adults: diagnosis, management, and health services development." Neuropsychiatr Dis Treat, Jul. 2016, 12:1669-86.
Nassar et al., "Improving the decision-making process in structural modification of drug candidates: reducing toxicity," Drug Discov Today, 9(24):1055-1064, (Dec. 2004).
Nassar et al., "Improving the decision-making process in the structural modification of drug candidates: enhancing metabolic stability," Drug Discov Today., 9(23)4020-1028, (Dec. 2004).
Nemeth et al., "Cariprazine versus risperidone monotherapy for treatment of predominant negative symptoms in patients with schizophrenia: a randomised, double-blind, controlled trial," Lancet., 389:1103-1113, Mar. 18, 2017.
Nyberg et al., "Positron emission tomography of in-vivo binding characteristics of atypical antipsychotic drugs. Review of D2 and 5-HT2 receptor occupancy studies and clinical response," Br. J. Psychiatry, Suppl., 29:40-44, (1996).
Oblak et al., "Reduced serotonin receptor subtypes in a limbic and a neocortical region in autism," Autism Res., Dec. 2013, 6(6):571-583.
Pacher and Kecskeméti, "Cardiovascular side effects of new antidepressants and antipsychotics: new drugs, old concerns?" Curr. Pharm, Des., 10(20):2463-2475, (2004).
Papp and Wieronska, "Antidepressant-like activity of amisulpride in two animal models of depression," J. Psychopharmacol., 14:46-52, (2000).
PCT International Preliminary Report on Patentability in International Appln. No. PCT/IB2018/054227, dated Dec. 17, 2019, 8 pages.
PCT International Search Report and Written Opinion in International Appln. No. PCT/IB2018/054227, dated Sep. 20, 2018, 12 pages.
PCT International Search Report and Written Opinion in International Appln. No. PCT/US2009/50835, dated Sep. 10, 2009, 9 pages.
PCT International Search Report in International Appln. No. PCT/HU04/00056, dated Nov. 11, 2004.
PCT International Search Report in International Appln. No. PCT/IB2017/054094, dated Oct. 26, 2017, 7 pages.
Penagarikano et al., "Absence of CNTNAP2 leads to epilepsy, neuronal migration abnormalities, and core autism-related deficits," Cell, Sep. 2011, 147(1):235-246.
Persico and Napolioni, "Autism genetics," Behav. Brain Res., Aug. 2013, 251:95-112.
Pilla et al., "Selective inhibition of cocaine-seeking behaviour by a partial dopamine D3 receptor agonist," Nature, 400:371-375, (1999).
Posey et al., "Developing drugs for core social and communication impairment in autism." Child Adolesc. Psychiatr, Clin. N. Am., Oct. 2008, 17(4):787-801.
Preechagoon et al., "Improved Dissolution Rate of Poorly Soluble Drug by Incorporation of Buffers," Drug Development and Industrial Pharmacy., 2000, 26(8): 891-894.
Rabinowitz et al., "Negative symptoms in schizophrenia—the remarkable impact of inclusion definitions in clinical trials and their consequences," Schizophrenia Research, 2013, 150:334-338.
Reavill et al., "Pharmacological actions of a novel, high-affinity, and selective human dopamine D(3) receptor antagonist, SB-277011-A," J Pharmacol Exp Ther., 294(3):1154-1165, (Sep. 2000).
Rógoz et al., "Anxiolytic-like effect of nafadotride and PNU 99194A, dopamine D3 receptor antagonists in animal models," Pol J Pharmacol., 52(6):459-462, (2000).
Russell, "Neurobiology of animal models of attention-deficit hyperactivity disorder," J. Neurosci. Methods 161:185-198, (2007).
S. H. Kim, et al., "Preparation method of 4-biphenylacetic acid with high yield and high purity," Database WPI Week 200648, Thomson Scientific, London AN 206-468774, XP0-02581633.
Sachs, "Unmet clinical needs in bipolar disorder," J. Clin. Psychopharmacol., 2003, 23(3 Suppl 1):S2-S8.
Sautel et al., "Nafadotride, a potent preferential dopamine D3 receptor antagonist, activates locomotion in rodents," J. Pharmacol. Exp, Ther., 1995, 275:1239-1246.
Schneider and Przewlocki, "Behavioral alterations in rats prenatally exposed to valproic acid: animal model of autism," Neuropsychopharmacology, Jan. 2005, 30(1):80-89.
Schwartz et al., "Dopamine D3 receptor: basic and clinical aspects," Clin. Neuropharmacol., 1993, 16(4):295-314.
Schwartz et al., "Possible implications of the dopamine D(3) receptor in schizophrenia and in antipsychotic drug actions," Brain Res. Rev., Mar. 2000, 31(2-3):277-287.
Seeman, "Dopamine D2 receptors as treatment targets in schizophrenia," Clin Schizophr Relat Psychoses., 4(1):56-73, (Apr. 2010).
Seeman, "Antipsychotic drugs, dopamine receptors and schizophrenia," Clin. Neurosci. Res., 1:53-60, (2001).
Seeman, "Brain dopamine receptors" Pharmacological Reviews, 32(3): 229-313 (1980).
Shafer and Levant, "The D3 dopamine receptor in cellular and organismal function," Psychopharmacology (Berl), v, 135:1-16, (1998).
Shahid et al., "Asenapine: a novel psychopharmacologic agent with a unique human receptor signature," J. Psychopharmacol., Jan. 2009, 23(1):65-73.
Shalev et al., "Neurobiology of relapse to heroin and cocaine seeking: a review.," Pharmacol. Rev. 54 (1), 1-42, (2002).
Shapiro et al., "Aripiprazole, a novel atypical antipsychotic drug with a unique and robust pharmacology," Neuropsychopharmacology, Aug. 2003, 28(8):1400-1411.
Siegel and Rathbone, Chapter 2: Overview of Controlled Release Mechanisms, Fundamentals and Applications of Controlled Release Drug Delivery, 2011, Siepmann et al. eds., 25 pages.
Sigala et al., "Opposite effects of dopamine $D_2$ and $D_3$ receptors on learning and memory in the rat," Eur. J. Pharmacol., 336:107-112, (1997).

(56) References Cited

OTHER PUBLICATIONS

Smith et al., "Maximizing response to first-line antipsychotics in schizophrenia: a review focused on finding from meta-analysis," Psychopharmacology, Feb. 2019, 236(2):545-549.
Smith et al., "The dopamine D3/D2 receptor agonist 7-OH-DPAT induces cognitive impairment in the marmoset," Pharmacol. Biochem. Behav., 63:201-211, (1999).
Sokoloff et al., "Molecular cloning and characterization of a novel dopamine receptor (D3) as a target for neuroleptics," Nature, 1990, 347(6289):146-151.
Souillac, et al., Characterization of Delivery Systems, Differential Scanning Calorimetry, pp. 217-218 (in Encyclopedia of Controlled Drug Delivery, 1999, John Wiley & Sons, pp. 212-227), (1999).
Stahl and Grady, "A critical review of atypical antipsychotic utilization: comparing monotherapy with polypharmacy and augmentation," Curr. Med. Chem., 11:313-327, (2004).
Stahl, Essential Psychopharmacology: Neuroscientific Basis and Practical Applications, 2nd ed., p. 409, Cambridge University Press, pp. 409-414, (2000).
Steiner et al., "D3 dopamine receptor-deficient mouse: evidence for reduced anxiety," Physiol Behav., 63(1):137-141, print 1998, (1997).
Stemp et al., "Design and synthesis of trans-N-[4-[2-(6-cyano-1,2,3,4-tetrahydroisoquinolin-2-yl)ethyl]cyclohexyl]-4-quinolinecarboxamide (SB-277011): A potent and selective dopamine D(3) receptor antagonist with high oral bioavailability and CNS penetration in the rat," J. Med. Chem., 43(9):1878-1885, (2000).
Szekely et al., "Genotoxic Impurities in Pharmaceutical Manufacturing: Sources, Regulations, and Mitigation," Chemical Review, Aug. 2012, 4 pages.
Tada et al., "Combined treatment of quetiapine with haloperidol in animal models of antipsychotic effect and extrapyramidal side effects: comparison with risperidone and chlorpromazine," Psychopharmacology, 2004, 176(1):94-100.
Tadori et al., "In vitro pharmacology of aripiprazole, its metabolite and experimental dopamine partial agonists at human dopamine D2 and D3 receptors," Eur. J. Pharmacol., Oct. 2011, 668(3):355-365.
Teng et al., "Reversal of social deficits by subchronic oxytocin in two autism mouse models," Neuropharmacology, Jun. 2016, 105:61-71.
Thanos et al., "The effects of two highly selective dopamine D3 receptor antagonists (SB-277011A and NGB-2904) on food self-administration in a rodent model of obesity," Pharmacol Biochem Behav. 89: 499-507, (2008).
Torisawa et al., "Progress in arylpiperazine synthesis by the catalytic amination reaction," Bioorganic and Medicinal Chemistry, Dec. 2002, 10(12)4023-4027.
Ukai et al., "Effects of the dopamine D3 receptor agonist, R(+)-7-hydroxy-N,N-di-n-propyl-2-aminotetralin, on memory processes in mice," Eur. J. Pharmacol., 1997, 324:147-151.
Ulrich, "Crystallization," Kirk-Othmer Encyclopedia of Chemical Technology, 2002, Chapter 4, 7 pages.
Vahia, "Diagnostic and statistical manual of mental disorders 5: A quick glance," Indian J. Psychiatry, Jul. 2013, 55(3):220-3.
Van Aerde et al., "In vitro evaluation of modified starches as matrices for sustained release dosage forms," International Journal of Pharmaceutics, Jul. 1988, 45:145-152.
Van der Kooij and Glennon, "Animal models concerning the role of dopamine in attention-deficit hyperactivity disorder," Neuroscience and Biobehavioral Reviews, 2007, 31: 597-618.
Vanderschuren and Trezza, "What the laboratory rat has taught us about social play behavior: role in behavioral development and neural mechanisms," Curr. Top Behav. Neurosci., 2013, 16:189-212.
Vippagunta et al., "Crystalline solids," Adv Drug Deliv Rev., 48(1):3-26, (May 16, 2001).
Waters et al., "Differential effects of dopamine D2 and D3 receptor antagonists in regard to dopamine release, in vivo receptor displacement and behavior," J. Neural. Transm. Gen. Sect., 98:39-55, (1994).
West, "Solid Solutions," Solid State Chemistry and Its Applications, Wiley, Chapter 10, pp. 358, pp. 365 (1988).
Willner et al., "Dopaminergic mechanism of antidepressant action in depressed patients," J. Affective Disorders 86: 37-45, (2005).
Wong and Van Tol, "Schizophrenia: from phenomenology to neurobiology," Neurosci. Biobehav. Rev., 27(3):269-306, (2003).
World Health Organization, The World Health Report 2001; Mental Health: New Understanding, New Hope, http://www.who.int/whr/2001/en/2001, 169 pages (2001).
Wustrow et al., "Aminopyrimidines with High Affinity for Both Serotonin and Dopamine Receptors," J. Med. Chem., 1998, 41:760-771.
Wyatt and Henter, "An economic evaluation of manic-depressive illness—1991," Soc. Psychiatry Psychiatr, Epidemiol., 30(5):213-219, (1995).
Youdim, "The path from anti Parkinson drug selegiline and rasagiline to multifunctional neuroprotective anti Alzheimer drugs ladostigil and m30," Curr Alzheimer Res., 2006, 3(5):541-550.
Young et al., "A rating scale for mania: reliability, validity and sensitivity," The British Journal of Psychiatry, 1978, 133:429-435.
Zink et al., "Combination of amisulpride and olanzapine in treatment-resistant schizophrenic psychoses," Eur. Psychiatry, 2004, 19:56-58.
International Preliminary Report on Patentability in International Application No. PCT/IB2013/060465, dated Jun. 11, 2015, 4 pages.
International Search Report and Written Opinion in International Application No. PCT/IB2013/060465, dated Jan. 22, 2014, 6 pages.
Arban et al., "Evaluation of the effects of lamotrigine, valproate and carbamazepine in a rodent model of mania," Behavioural brain research, Mar. 7, 2005, 158(1):123-132.
El-Mallakh et al., "Cariprazine delays ouabain-evoked epileptiform spikes and loss of activity in rat hippocampal slices," Psychiatry Research, Sep. 30, 2015, 229(1-2):370-373.
Gao et al., "Cariprazine exerts antimanic properties and interferes with dopamine D2 receptor (β-arrestin interactions," Pharmacology Research & Perspectives, Feb. 2015, 3(1):e00073, 10 pages.
Herman et al., "Mimicking human bipolar ion dysregulation models mania in rats," Neuroscience & Biobehavioral Reviews, Jan. 1, 2007, 31(6):874-881.
Mack et al., "Review of animal models of bipolar disorder that alter ion regulation," Neuroscience & Biobehavioral Reviews, Dec. 1, 2019, 107:208-214.
Retamales-Ortega et al., "P2C-Type ATPases and their regulation," Molecular neurobiology, Mar. 2016, 53(2):1343-1354.
Román et al., "Cariprazine alleviates core behavioral deficits in the prenatal valproic acid exposure model of autism spectrum disorder," Psychopharmacology, Sep. 2021, 238(9):2381-2392.

\* cited by examiner

CARBAMOYL CYCLOHEXANE DERIVATIVES FOR TREATING AUTISM SPECTRUM DISORDER

CROSS REFERENCE PARAGRAPH

This application claims priority to U.S. Provisional Application No. 62/831,981 filed Apr. 10, 2019, the contents of which are hereby incorporated by reference.

FIELD OF THE INVENTION

The present invention relates to trans-N-[4-[2-[4-(2,3-dichlorophenyl)piperazin-1-yl]ethyl]cyclohexyl]-N',N'-dimethylurea (cariprazine), its salts, close analogs, derivatives, pharmaceutical compositions, metabolites and combinations for use in the treatment of symptoms of autism spectrum disorder.

BACKGROUND OF THE INVENTION

Autism spectrum disorder (ASD) is a complex, very challenging and prevalent neurodevelopmental condition with frequencies as high as 1:34-1:77 (average 1:59) in the US pediatric population across eleven states in 2014 (*CDC Morbidity and Mortality Weekly Report Surveillance Summaries*, Apr. 27, 2018/67(6):1-23). Based on a number of epidemiological studies, the median of prevalence estimate of ASD was 62/10,000 in 2012 (Elsabbagh et al., *Autism Res.* 2012, 5:160-179). Thus, ASD is recognized today as a global, common, lifelong neurodevelopmental disorder that affects approximately 1% of both children and adults (Brugha et al., *Arch. Gen. Psychiatry.* 2011, 68:459-465; Murphy et al., *Neuropsychiatr. Dis. Treat.* 2016, 12:1669-1686).

The disorder is characterized by two core symptoms of socio-communicational dysfunctions as well as restricted (repetitive, stereotyped) behaviors and thinking (*Diagnostic and Statistical Manual of Mental Disorders*, Fifth Edition, pp. 50-59). Social impairments comprise abnormal social approach, failure of normal back-and-forth communication, failure to initiate and reciprocate interaction. Communicational deficits may include poorly integrated verbal and nonverbal communication, abnormal eye contact and body language, deficits in understanding gestures, lack of facial expressions. In general, deficits in developing, maintaining and understanding relationships, adjusting to social situations, sharing imaginative play and absence of interest in peers may be present. With respect to the other core symptom domain, stereotyped or repetitive motor movements, insistence on sameness and routines, highly fixated interests that are abnormal in intensity or focus and abnormal sensory reactivity can be identified.

In addition to the core symptoms, ASD is also often accompanied by associated or comorbid symptoms including intellectual disability, attention deficit, hyperactivity, mood disorders, seizures, sleep problems, etc. A further frequently associated symptom domain is irritability that comprises tantrums, aggression towards others, self-injurious behavior and mood swings.

The unmet medical need in ASD is enormous, since there is no pharmacological treatment currently available for the treatment of core symptoms in ASD. While there is no approved drug for the treatment of core symptoms, only two antipsychotics of the many available drugs of the same class—risperidone and aripiprazole—have been approved in the US Food & Drug Administration for the treatment of ASD-associated irritability in children, ages 5-16 years. Aripiprazole has also been approved for this purpose in Japan. Although large efforts have been put into clinical research, no effective pharmacological treatment has been identified until now to alleviate the core symptom domains of ASD.

Risperidone and aripiprazole are atypical antipsychotics with different receptor profiles in vitro. Whereas risperidone has been found to bind with high affinity to serotonin $5\text{-HT}_{2A}$ receptors and function as an antagonist of the receptor, aripiprazole displays high affinity for dopamine $D_2$, $D_3$, $5\text{-HT}_{1A}$ and $5\text{-HT}_{2B}$ receptors, and it behaves as a partial agonist at dopamine $D_2$, $D_3$ and serotonin $5\text{-HT}_{1A}$ receptors. (Shahid et al., *J. Psychopharmacol.* 2009, 23:65-73; Tadori et al. *Eur. J. Pharmacol.* 2011, 668:355-365; Shapiro et al., *Neuropsychopharmacol.* 2003, 28:1400-1411). It is important to note that both aripiprazole and risperidone occupy dopamine $D_2$ receptors in the human brain (Muly et al., *J. Pharmacol. Exp. Ther.* 2012, 341:81-89; Gründer et al., *Am. J. Psychiatry* 2008, 165:988-995). However, neither of the two compounds were found to demonstrate occupancy of dopamine $D_3$ receptors in humans (Graff-Guerrero et al., *Arch. Gen Psychiatry* 2009, 66:606-615).

Although risperidone and aripiprazole are used to treat ASD-associated irritability, these antipsychotic compounds are neither approved nor used to treat the core symptom domains of ASD. Results of clinical investigations with regards to the usefulness of risperidone and aripiprazole in the treatment of the core symptoms are contradictory, showing lack of efficacy for aripiprazole and mixed results for risperidone. Aripiprazole was investigated in open label trials and it did not improve the lethargy/social withdrawal subscale of the Aberrant Behavioral Checklist (Ichikawa et al., *Child Psychiary Hum. Dev.* 2017, 48:796-806; LeClerc et al., *Pharma. Ther.* 2015, 40:389-397; Posey et al., *Child Adolesc. Psychiatry Clin. N. Am.* 2008, 17:787-798). Studies with risperidone suggest that it may result in modest improvements of the core symptoms in children with pervasive developmental disorders exhibiting high levels of baseline irritability however, it is unclear whether risperidone improved these symptoms in the absence of irritability (LeClerc et al., *Pharma. Ther.* 2015, 40:389-397; Posey et al., *Child Adolesc. Psychiatry Clin. N. Am.* 2008, 17:787-798). Thus, for aripiprazole there is no support from human studies for its usefulness to treat socio-communicational dysfunction in ASD. In case of risperidone, there is also a lack of solid evidence for social behavioral efficacy in ASD subjects.

Pharmacodynamic effects of risperidone and aripiprazole have also been investigated in animal models of autism, and yielded mixed results. In a number of preclinical ASD mouse models, including the prenatal valproate model (Auclair et al., *World Congress of The International College of Neuropsychopharmacology* 2014, LP-03-011), the Cntnap2 knockout mice (Penagarikano et al., *Cell* 2011, 147:235-246), the NMDA receptor NR1 subunit hypomorph mice (Teng et al., *Neuropharmacology* 2016, 105:61-71) and the BTBR mouse strain (Chadman, *Pharm. Biochem. Behav.* 2011, 97:586-594) neither aripiprazole nor risperidone could improve the social behavior deficits. In another study, utilizing prenatal valproate treatment in mice, both risperidone and aripiprazole improved core behavioral deficits after chronic administration, while acute treatment was without effect (Hara et al., *Psychopharmacology* 2017, 234:3217-3228). Hara et al. discusses possible mechanisms behind the improvements of ASD-like symptoms due to chronic risperidone and aripiprazole treatment and emphasize the role of dopamine $D_1$ and $D_2$ receptor activation following dopamine release in the prefrontal cortex. The authors do not mention any role for dopamine $D_3$ receptors in the molecular mechanism whereby risperidone or aripiprazole may alleviate the behavioral effects of prenatal valproate treatment.

Patent application WO 2005/012266A1 discloses carbamoyl cyclohexane derivatives that are dopamine D3/D2 receptor partial agonists. Notably, WO 2005/012266A1 discloses trans-N-[4-[2-[4-(2,3-dichlorophenyl)piperazin-1-yl]ethyl]cyclohexyl]-N',N'- dimethylurea (cariprazine) corresponding to Formula 1 and its hydrochloride salt. As it was later established, cariprazine (US: Vraylar®, Europe: Reagila®) is a dopamine $D_3$-preferring $D_3/D_2$ receptor and serotonin 5-$HT_{1A}$ receptor partial agonist (Kiss et al., *J. Pharmacol. Exp. Therap.* 2010, 333:328-340) that has been approved to treat schizophrenia (US and Europe) and manic or mixed episodes associated with bipolar I disorder (US). Active metabolites of cariprazine include, not exclusively, desmethyl cariprazine and didesmethyl cariprazine (WO 2008/142461A1). Additional patent applications describe the hydrochloride salt of cariprazine (WO 2008/139235A2) and the deuterized derivative of cariprazine (WO 2011/060363A2).

WO 2005/012266A1 also discloses close analogs of cariprazine that are listed on page 21-22 of the said patent application. These close analogs also include trans-N-(4-{2-[4-(2,3-dichloro-phenyl)-piperazine-1-yl]-ethyl}-cyclohexyl)-morpholine-4 carboxamide (Compound 2).

Compound 1

Compound 2

Among the diseases to be treated and/or prevented by the carbamoyl cyclohexane derivatives, WO 2005/012266A1, WO2008/139235A2, WO2008/141135A1, WO2009/020897A1 and WO2010/009309A1 claim the treatment of autism as such. As mentioned above, ASD is a very complex disorder with regard to its manifestation in human patients; its core symptoms include socio-communicational impairments and restricted/repetitive behaviors with variable severity as well as a great variety of comorbid symptoms. The selected ASD-associated symptoms defined hereafter were neither specified nor supported by any scientific evidence in the aforementioned patent applications. These symptoms specifically include socio-communicational impairments, restricted and repetitive behaviors, attention deficit and hyperactivity, as well as irritability.

Compared to risperidone and aripiprazole, cariprazine has a unique receptor profile (Shahid et al., *J. Psychopharmacol.* 2009, 23:65-73; Kiss et al., *J. Pharmacol. Exp. Therap.* 2010, 333:328-340). Cariprazine shows subnanomolar affinity for the dopamine $D_3$, $D_{2L}$ and $D_{2S}$ receptors ($K_i$ values of 0.09, 0.5 and 0.7 nM, respectively) with an approximately 8-fold preference for the dopamine $D_3$ versus $D_2$ receptor. Functionally, the compound is a partial agonist at the dopamine $D_3$ and $D_2$ receptors. In addition, cariprazine shows nanomolar affinity for the serotonin 5-$HT_{2B}$ and 5-$HT_{1A}$ receptors ($K_i$ 0.6 and 2.6 nM, respectively) where it acts as full antagonist and weak partial agonist, respectively. The close analog of cariprazine (Compound 2) shows a very similar molecular pharmacological profile to cariprazine. It has also subnanomolar affinity for the dopamine $D_3$, $D_{2L}$ and $D_{2S}$ receptors ($K_i$ 0.17, 0.4 and 0.52 nM, respectively). Functionally, Compound 2 is a partial agonist at the dopamine $D_3$ and $D_2$ receptors. In addition, Compound 2 shows nanomolar affinity for the serotonin 5-$HT_{2B}$ and 5-$HT_{1A}$ receptors ($K_i$ 1.11 and 5.73 nM, respectively), where it acts as full antagonist and weak partial agonist, respectively. When taking into account this combination of receptorial affinities and functionalities, cariprazine and its close analog (Compound 2) are special and clearly different from other available antipsychotics.

Although results of genetic association studies available at that time (Martineau et al., *Dev. Med. Child Neurol.* 1994, 36:688-697; Persico and Napolioni, *Behav. Brain Res.* 2013, 251:95-112) did not imply the dopamine $D_3$ receptors in the pathomechanism of ASD, researchers of Pierre Fabre Medicament investigated as first ones a dopamine $D_3$ receptor antagonist and found it effective in an animal model of ASD. Pierre Fabre Medicament filed a patent application (WO 2015/086836A1) related to a chromone derivative for its use as medicament for the treatment of ASD. The chromone derivative in WO 2015/086836A1 is a dopamine $D_3$ receptor full antagonist lacking any intrinsic activity revealed by a MAP kinase activity test on human recombinant dopamine $D_3$ receptors. The chromone derivative of that invention was shown to improve impaired social behavior of rats that had been exposed to sodium valproate during their intrauterine life. Despite its beneficial effects in the above animal model of ASD, there is no available clinical evidence up to now that the chromone compound disclosed in the patent application WO 2015/086836A1 or related compounds are useful for the treatment of this disorder in human patients.

Whereas cariprazine is a partial agonist at dopamine $D_2$ and $D_3$ receptors (Kiss et al., *J. Pharmacol. Exp. Therap.* 2010, 333:328-340; Tadori et al. *Eur. J. Pharmacol.* 2011, 668:355-365), and according to WO 2015/086836A1 the chromone derivatives by Pierre Fabre Medicament patent are defined as dopamine $D_3$ antagonists, therefore a skilled person in the art would not consider the two compounds to have similar effect.

First, there is clear difference between the chemical structures. The structural differences between the two base compounds have consequences on differences in physicochemical properties, molecular pharmacological, pharmacodynamic and pharmacokinetic properties.

Second, while the Pierre Fabre compound produced no stimulatory activity in a cellular system (ERK1/2 phosphorylation assay) (Heusler et al., *Eur. Neuropsychopharm.* 2016, 26(S2):S490-S491), cariprazine stimulated ERK1/2 phosphorylation in Chinese hamster ovary cells expressing the D$_3$ receptor (unpublished data, data in company file). This implies that the two compounds behave completely differently in in vitro functional assays.

Third, the two compounds have different receptor profiles (Heusler et al., *Eur. Neuropsychopharm.* 2016, 26(S2):S490-S491; Kiss et al., *J. Pharmacol. Exp. Therap.* 2010, 333: 328-340). The Pierre Fabre chromone derivative has subnanomolar affinity for the dopamine D$_3$ receptor (K$_i$ 0.16 nM), nanomolar affinities for the dopamine D$_{2L}$ and D$_{2S}$ receptors (K$_i$ 12.6 and 6.3 nM, respectively). Thus, there is a greater preference for the dopamine D$_3$ receptors versus D$_2$ receptors in case of the Pierre Fabre compound than in case of cariprazine. The chromone derivative has considerable serotonin 5-HT$_{1A}$ receptor affinity (Ki 0.13 nM), while cariprazine shows lower affinity for this receptor (Ki 2.6 nM). Cariprazine, its close analog (Compound 2) and the Pierre Fabre compound are all partial agonists of the serotonin 5-HT$_{1A}$ receptor however, while the Pierre Fabre chromone derivative has substantial intrinsic activity (57-75%) (Heusler et al., *Eur. Neuropsychopharm.* 2016, 26(S2): S490-S491), both cariprazine and Compound 2 are only weak partial agonists with intrinsic activities of 38 and 30%, respectively (Kiss et al., *J. Pharmacol. Exp. Therap.* 2010, 333:328-340, and unpublished adat, data in company file).

As mentioned above, cariprazine has a special receptor profile comprising dopamine D$_3$/D$_2$ receptor partial agonism, weak serotonin 5-HT$_{1A}$ receptor partial agonism and serotonin 5-HT$_{2B}$ receptor full antagonism. Lim et al. found that treatment of Fmr1 knock-out mice with the selective serotonin 5-HT$_{2B}$ receptor agonist BW723C86 resulted in the improvement of cognitive abilities (Lim et al., *Gene. Dev.* 2014, 28:273-289). Further studies reported that there is also reduced function of serotonin 5-HT$_2$ type (not-specified) receptors in the periphery and brain of ASD patients (McBride et al., *Arch. Gen. Psychiatry* 1989, 46, 213-221). Taking the above results into account it is not expected that a serotonin 5-HT$_{2B}$ receptor antagonist such as cariprazine would be effective in an animal model of ASD.

Moreover, Oblak et al. (*Autism Res.* 2013, 6:571-583) found significantly reduced serotonin 5-HT$_{1A}$ receptor binding in post mortem cortical samples of subjects with autism in two regions of a limbic-cortical network that contribute to social-emotional behaviors. Given these reduced serotonin 5-HT$_{1A}$ receptor levels, it is unlikely that a weak partial agonist such as cariprazine at these receptors would be effective in an ASD model.

Along with the need to treat autism in general, there is also a need to treat one or more symptoms of autism. Furthermore, there is a need to treat conditions such as Asperger's syndrome, atypical autism (otherwise known as pervasive developmental disorder not otherwise specified; PDD-NOS), Rett syndrome, childhood disintegrative disorder, attention deficit hyperactivity disorder (ADHD) and sensory integration dysfunction.

SUMMARY OF THE INVENTION

In one aspect, the present application relates to trans-N-[4-[2-[4-(2,3-dichlorophenyl)piperazin-1-yl]ethyl]cyclohexyl]-N',N'-dimethylurea (cariprazine), its salts, close analogs, derivatives, pharmaceutical compositions, metabolites and combinations for use in the treatment of symptoms of autism spectrum disorder. In another aspect, the application relates to the use of cariprazine, its salts, close analogs, derivatives, pharmaceutical compositions, metabolites and combinations for the treatment of conditions selected from Asperger's syndrome, atypical autism (otherwise known as pervasive developmental disorder not otherwise specified; PDD-NOS), Rett syndrome, childhood disintegrative disorder, attention deficit hyperactivity disorder (ADHD), Pathological Demand Avoidance (PDA), Fragile X Syndrome (FXS), Angelman Syndrome, Tuberous Sclerosis Complex, Phelan McDermid Syndrome and sensory integration dysfunction.

DETAILED DESCRIPTION OF THE INVENTION

In one aspect, the present application relates to trans-N-[4-[2-[4-(2,3-dichlorophenyl)piperazin-1-yl]ethyl]cyclohexyl]-N',N'-dimethylurea hydrochloride (cariprazine) and trans-N-(4-{2-[4-(2,3-dichloro-phenyl)-piperazine-1-yl]ethyl}-cyclohexyl)-morpholine-4 carboxamide hydrochloride (Compound 2) disclosed in WO 2005/012266A1. Cariprazine showed great benefit in an animal model for the symptoms of ASD. These result indicate that cariprazine, its close analogs and its derivatives may be of therapeutic use against the symptoms of ASD in human patients.

In one aspect, the application relates to the use of cariprazine, its salts, close analogs, derivatives, pharmaceutical compositions, metabolites and combinations for the treatment of conditions selected from Asperger's syndrome, atypical autism (otherwise known as pervasive developmental disorder not otherwise specified; PDD-NOS), Rett syndrome, childhood disintegrative disorder, attention deficit hyperactivity disorder (ADHD), Pathological Demand Avoidance (PDA), Fragile X Syndrome (FXS), Angelman Syndrome, Tuberous Sclerosis Complex, Phelan McDermid Syndrome and sensory integration dysfunction.

In a preferred embodiment, cariprazine or a pharmaceutically acceptable salt thereof is used for the treatment of persistent deficits in social communication and social interactions associated with ASD; for the treatment of restrictive or repetitive behaviors associated with ASD; for the treatment for stereotyped or repetitive movements associated with ASD; and/or as a treatment for deficits in social-emotional reciprocity associated with ASD.

In a preferred embodiment, cariprazine or a pharmaceutically acceptable salt thereof is used for the treatment of one or more symptoms of ASD selected from social communication deficits, restricted interests and repetitive behaviors. In some embodiments, cariprazine or a pharmaceutically acceptable salt thereof is used for the treatment of one or more symptoms of ASD selected from restricted, repetitive, and stereotyped patterns of behaviors, interests and activities.

Cariprazine and Compound 2 were investigated in the prenatal valproate model of ASD. As described in the Examples, cariprazine hydrochloride and Compound 2 hydrochloride were able to reverse behavioral deficits in rats that had been exposed to valproate during their intrauterine life. The results show that the above two compounds are suitable to treat symptoms of ASD.

In another preferred embodiment, the present application is directed to the use of trans-N-[4-[2-[4-(2,3-dichlorophenyl)piperazin-1-yl]ethyl]cyclohexyl]-N',N'-dimethylurea and/or its close analogs and/or its derivatives and/or its metabolites and/or pharmaceutically acceptable salts thereof for the treatment of socio-communicational deficits as core symptom of autism spectrum disorder.

In another preferred embodiment, the present application is directed to the use of trans-N-[4-[2-[4-(2,3-dichlorophenyl)piperazin-1-yl]ethyl]cyclohexyl]-N',N'-dimethylurea and/or its close analogs and/or its derivatives and/or its metabolites and/or pharmaceutically acceptable salts thereof for the treatment of restricted and repetitive behaviors as core symptom of autism spectrum disorder.

In another preferred embodiment, the present application is directed to the use of trans-N-[4-[2-[4-(2,3-dichlorophenyl)piperazin-1-yl]ethyl]cyclohexyl]-N',N'-dimethylurea and/or its close analogs and/or its derivatives and/or its metabolites and/or pharmaceutically acceptable salts thereof for the treatment of irritability associated with autism spectrum disorder.

In another preferred embodiment, the present application is directed to the use of trans-N-[4-[2-[4-(2,3-dichlorophenyl)piperazin-1-yl]ethyl]cyclohexyl]-N',N'-dimethylurea and/or its close analogs and/or its derivatives and/or its metabolites and/or pharmaceutically acceptable salts thereof for the treatment of attention deficit and hyperactivity associated with autism spectrum disorder.

In another preferred embodiment the application relates to a pharmaceutical composition defined above, wherein the core symptoms of autism spectrum disorder are sociocommunicational deficits.

In another preferred embodiment the application relates to a pharmaceutical composition defined above, wherein the core symptoms the core symptoms of autism spectrum disorder are restricted and repetitive behaviors.

In another preferred embodiment the application relates to a pharmaceutical composition defined above, wherein the condition to be treated is irritability associated with autism spectrum disorder.

In another preferred embodiment the application relates to a pharmaceutical composition defined above, wherein the condition to be treated is attention deficit and hyperactivity associated with autism spectrum disorder.

The present application also relates to the method of treating autism spectrum disorder wherein the method comprises the administration of the pharmaceutical compositions defined above.

The compositions according to the present application can be administered by the oral, transdermic, parenteral, intranasal and rectal routes. The compositions can especially be administered by the oral route in an appropriate formulation. The dosages of the compound (trans-N-[4-[2-[4-(2,3-dichlorophenyl)piperazin-1-yl]ethyl]cyclohexyl]-N',N'- dimethylurea) or its close analog, salts, derivative, or metabolite in the compositions of the application can be adjusted to obtain an amount of active substance that results in the desired therapeutic response. Therefore, the dosage level depends on the desired therapeutic response, the route of administration, the expected duration of treatment and other factors such as age, gender or body weight of the patient. The dosages can be from 0.01 to 12 mg daily and can be titrated to effect.

Cariprazine may also be used in combination with at least one other active ingredient that have been already in use for the treatment of comorbid symptoms of ASD (e.g., psychostimulants, antipsychotics, antidepressants, anxiolytics, antihypertensives, antiepileptics, narcotics, spasmolytics or other agents).

Psychostimulants include, but not limited to, centrally acting sympathomimetics (amphetamine, methylphenidate, modafinil, atomoxetine), nootropics or other psychostimulants (vinpocetine, donepezil, memantine).

Antipsychotics include, but not limited to, typical and atypical antipsychotics, such as haloperidol, pimozide, clozapine, olanzapine, quetiapine, sertindole, ziprasidone, lurasidone, risperidone, aripiprazole, brexpiprazole, iloperidone, paliperidone, lithium.

Antidepressants include, but not limited to, non-selective monoamine reuptake inhibitors (desipramine, imipramine, clomipramine, amitriptyline, nortriptyline), serotonin modulator and stimulators (vilazodone, vortioxetine), selective serotonin reuptake inhibitors (fluoxetine, paroxetine, sertraline, fluvoxamine, citalopram, escitalopram), non-hydrazide monoamine oxidase inhibitor (moclobemide,) or other agents (mianserin, trazodone, nefazodone, mirtazapine, tianeptine, venlafaxine, milnacipran, reboxetine, duloxetine, agomelatine, bupropion, gepirone).

Anxiolytics include, but not limited to, benzodiazepines (diazepam, chlorodiazepoxide, oxazepam, lorazepam, alprazolam), azaspirode-diones (buspirone).

Antihypertensives include, but not limited to, imidazoline receptor agonists (clonidine, guanfacine) and a combination of these substances with a diuretic.

Antiepileptics include, but not limited to, barbiturates and their derivatives (phenobarbital), hydantoin derivatives (phenytoin), succinimide derivatives (ethosuximide), benzodiazepine derivative clonazepam, carboxamide derivatives (carbamazepine, oxcarbazepine), fatty acid derivatives (valproic acid, valpromide, vigabatrin, tiagabine) and other antiepileptics (lamotrigine, topiramate, gabapentin, levetiracetam, zonisamide, pregabalin).

Narcotics include, but not limited to, barbiturates (pentobarbital), benzodiazepines (midazolam), cyclopyrrolone benzodiazepine derivatives (zopiclone, zolpidem), melatonin receptor agonists (melatonin, ramelteon).

Spasmolytics or antispasmodics include, but not limited to centrally acting agents (baclofen, arbaclofen, tolperisone) and papaverine.

Other agents include, but not limited to, medicinal products (probiotics, digestive aids/digestives, herbal extracts), vitamins (both water soluble and fat soluble, such as, but not limited to, vitamin A, D3, E, K, B1, B5, B6, B12, C or their derivatives) and nutritional supplements (coenzymes eg. Q10, flavonoids eg., resveratrol, lecithin, unsaturated fatty acids, including fatty acids $\omega 3$ and $\omega 6$).

Accordingly, the present invention also relates to a pharmaceutical composition for use in treating autism spectrum disorder comprising
1) trans-N-[4-[2-[4-(2,3-dichlorophenyl)piperazin-1-yl]ethyl]cyclohexyl]-N',N'-dimethylurea and/or its close analogs and/or its derivatives and/or its metabolites and/or pharmaceutically acceptable salts thereof and
2) at least one adjunctive therapeutical agent, which is selected from the group consisted of psychostimulants/nootropics, antipsychotics, antidepressants, anxiolytics, antihypertensives, antiepileptics, narcotics and spasmolytics and
3) one or more pharmaceutically acceptable carriers, diluents and excipients.

At the same time, the present application also relates to a pharmaceutical combination comprising trans-N-[4-[2-[4-(2,3-dichlorophenyl)piperazin-1-yl]ethyl]cyclohexyl]-N', N'-dimethylurea and/or its close analogs and/or its derivatives and/or its metabolites and/or pharmaceutically acceptable salts thereof and at least one adjunctive therapeutical agent for use in treating autism spectrum disorder.

In a preferred embodiment the present application relates to a pharmaceutical combination defined above, wherein at least one adjunctive therapeutical agent is selected from the group consisted of psychostimulants/nootropics, antipsychotics, antidepressants, anxiolytics, antihypertensives, antiepileptics, narcotics and spasmolytics.

In another preferred embodiment the present application relates to a pharmaceutical combination defined above, wherein psychostimulants/nootropics are selected from the list comprising amphetamine, methylphenidate, modafinil, atomoxetine, vinpocetine, donepezil and memantine.

In another preferred embodiment the present application relates to a pharmaceutical combination defined above, wherein antipsychotics are selected from the list comprising haloperidol, pimozide, clozapine, olanzapine, quetiapine, sertindole, ziprasidone, lurasidone, risperidone, aripiprazole, brexpiprazole, iloperidone, paliperidone and lithium.

In another preferred embodiment the present application relates to a pharmaceutical combination defined above, wherein antidepressants are selected from the list comprising desipramine, imipramine, clomipramine, amitriptyline, nortriptyline, vilazodone, vortioxetine, fluoxetine, paroxetine, sertraline, fluvoxamine, citalopram, escitalopram moclobemide, mianserin, trazodone, nefazodone, mirtazapine, tianeptine, venlafaxine, milnacipran, reboxetine, duloxetine, agomelatine, bupropion and gepirone.

In another preferred embodiment the present application relates to a pharmaceutical combination defined above, wherein anxiolytics are selected from the list comprising diazepam, chlorodiazepoxide, oxazepam, lorazepam, alprazolam and buspirone.

In another preferred embodiment the present application relates to a pharmaceutical combination defined above, wherein antihypertensive is selected from clonidine and guanfacine.

In another preferred embodiment the present application relates to a pharmaceutical combination defined above, wherein antiepileptics are selected from the list comprising phenobarbital, phenytoin, ethosuximide, clonazepam, carbamazepine, oxcarbazepine, valproic acid, valpromide, vigabatrin, tiagabine, lamotrigine, topiramate, gabapentin, levetiracetam, zonisamide and pregabalin.

In another preferred embodiment the present application relates to a pharmaceutical combination defined above, wherein narcotics are selected from the list comprising pentobarbital, midazolam, zopiclone, zolpidem, melatonin and ramelteon.

In another preferred embodiment the present application relates to a pharmaceutical combination defined above, spasmolytics are selected from the list comprising baclofen, arbaclofen, tolperisone and papaverine.

In one embodiment, cariprazine or a pharmaceutically acceptable salt thereof, is used for the treatment of a pediatric patient of age between about 5 to 12; or an adolescent patient of age between about 13 to 17; or an adult patient of age about 18 or above.

Preparation of Pharmaceutical Compositions

The following formulation examples illustrate representative pharmaceutical compositions of this application. The present application includes the following pharmaceutical compositions.
A) Solid oral dosage forms
  a. Tablets
  b. Capsules
  c. Granules
B) Liquid oral dosage forms
  a. Syrups
C) Other dosage forms
  a. Suppositories
  b. Transdermal patches
  c. Nasal sprays, aerosols Definitions The term "affinity" means the attraction of a drug for a biological target; it is a chemical term used to quantify the strength of drug-target interaction.

The term "full agonist" means a compound that produces the full maximal response of the biological system The term "partial agonist" means a compound that associates with a receptor and have only partial efficacy at the receptor relative to a full agonist.

The term "antagonist" means a compound that associates with a receptor and produces no response or prevents the response generated by an agonist of the same receptor.

The term "close analog" means compounds that are related to a compound based on their similarity of chemical structure as well as their in vitro pharmacological profile.

The term "salt" means nontoxic base addition salts of the compounds of the invention which are generally prepared by reacting the acid with a suitable organic or inorganic base.

The term "active metabolite" means such metabolites produced by different routes of biotransformation whose biological activity is similar to that of the parent compound.

The term "derivative" means such compounds that have been produced by chemical modification of cariprazine and its close analogs resulting not exclusively in prodrugs, deuterated compounds, bioisosters, etc.

The term "active ingredient" means cariprazine, its close analogs, salts, active metabolites and derivatives.

The term "pharmaceutically acceptable" describes an ingredient that is useful in preparing a pharmaceutical composition and is generally safe, non-toxic and neither biologically nor otherwise undesirable, and includes those acceptable for human pharmaceutical use.

The term "pharmaceutical composition" refers to a mixture of a compound of the invention with other chemical components, such as pharmaceutically acceptable excipients e.g. diluents or carriers. The pharmaceutical composition facilitates administration of the compound to the subject.

The term "excipient" defines a chemical compound that facilitates the incorporation of a compound into cells or tissues.

"Core symptoms" include socio-communicational dysfunctions and as well as restricted (repetitive, stereotyped) behaviors and thinking as described in the Diagnostic and Statistical Manual of Mental Disorders, Fifth Edition (2013).

The term "comorbid symptoms" means symptoms that may be associated with ASD, but are not core symptoms according to the Diagnostic and Statistical Manual of Mental Disorders, Fifth Edition (2013).

As used herein, the term "treatment" means using an effective therapy to reduce, alleviate or eliminate the symptoms associated with ASD.

The term "patient" refers to a human who received an ASD diagnosis.

The Prenatal Valproate Model

Prenatal valproate (valproic acid, VPA) exposure is known to increase the risk of ASD in humans (Christensen et al, *JAMA* 2013, 309). VPA exposure during intrauterine life in rodents is also known to lead to autistic-like phenotype in the offspring (Roullet et al, *Neurotox. Teratol.* 2013, 36, 45-56). VPA in rodents is administered typically around the 12th day of embryonic development when the closure of the neural tube and establishment of cranial nerve nuclei and the cerebellum occurs. The histone deacetylase inhibitory effect of VPA interferes with the above mentioned developmental steps and thereby brings about the autistic-like phenotype in the offspring. The autistic-like phenotype comprises—not exclusively—impaired communication in rat pups, impaired social play behavior in adolescent rats, hyperactivity, excessive stereotypical behavior and defective sociability in the 3-chamber assay in adult rats. Since the physiological origin and the symptoms of the prenatal VPA model show a good match with the human condition, this is a widely accepted rodent model of ASD with high translational value.

As described above, the prenatal VPA model has excellent construct and face validity, therefore it is a widely accepted disease model of ASD. In this method, time-mated female Wistar rats are administered a single dose of VPA (300-600 mg/kg, i.p.) on gestational day 12.5. Offspring are housed according to standard laboratory conditions until time of behavioral testing. Animals are housed in groups of 4 in conventional cages and maintained at 22-24° C. on a standard 12 hour light/dark cycle, with food and water available ad libitum. After investigational drug treatment, offspring are examined behaviorally in tests relevant for the assessment of autistic behavior. These tests include maternal deprivation-induced ultrasonic vocalization in rat pups, social play, social preference and the open field.

Maternal deprivation-induced ultrasonic vocalization in rat pups is a readout of socio-communicational function that is impaired in offspring after prenatal exposure to VPA (Gandal et al., Biol. Psychiatry 2010, 68, 1100-1106). To induce ultrasonic calls, prenatally VPA treated rat pups are placed individually into a cage where calls are being recorded with bat microphones. Calls are digitized with an audio filter and ultrasonic vocalization is recorded and quantified with SonoTrack software (Metris by. The Netherlands). Baseline vocalization is measured on postnatal days 11-12 days for 10 min. Animals are divided into homogenous groups based on baseline vocalizations. On postnatal day 13, animals are treated p.o. with the appropriate doses of drugs or vehicle 60 min before measurement and then returned to their nests until recording. Ultrasonic call counts are recorded for 10 min. Statistical analysis is performed on ultrasonic call counts with the non-parametric Kruskal-Wallis test and the post hoc Dunnett test.

Social play is a type of social interaction that is highly typical of adolescent mammals including rodents as well as humans (Vanderschuren and Trezza, Curr. Topics Behav. Neurosci. 2014, 16:189-212). Social play behavior is indicative of social functioning in adult life and is defective after prenatal VPA treatment in the offspring (Schneider and Przewlocki Neuropsychopharmacology 2005, 30:80-89). At postnatal day 30, following 8 days treatment with the test compound, prenatally VPA-treated rats are evaluated for juvenile play behavior. The test is carried out in a novel test arena with pairs of animals from the same treatment group over a 15-min trial. Animals are scored for play activity measured by duration of social play behavior. Statistical analysis employs one-way ANOVA and the post hoc Dunnett test.

The social preference in a 3-chamber apparatus is another indicator of intact social behavior in rats. The preference of a conspecific over an inanimate object as well as the ability to distinguish between familiar and novel conspecifics are necessary for normal social functioning and are defective in the prenatal VPA model in rats (Bambini-Junior et al., Brain Res. 2011, 1408:8-16). Social preference and social recognition memory are investigated in a 3-chamber apparatus. On postnatal day 59, prenatally VPA-treated rats are assessed for their social preference following 8 days of per os treatment with the test compound. On postnatal day 60, the same rats are assessed for their social recognition memory after 9 days of per os treatment with the test compound. Statistical analysis is performed by using two-way ANOVA, Student's t test and Dunnett test.

Beside socio-communicational impairments, repetitive behaviors are the other core symptom domain of ASD. Hyperactivity and excessive repetitive behaviors have been found in animals that were exposed to VPA during their intrauterine life (Schneider and Przewlocki Neuropsychopharmacology 2005, 30:80-89). At postnatal day 31-32, animals are scored for locomotor activity and exploratory behavior in a 10-min trial in an open field test arena after 9-day oral treatment with the test compound. Activity is analysed for readouts of repetitive/stereotypic behaviors such as total distance moved and frequency of circling behavior. Statistical analysis employs one-way ANOVA and the post hoc Dunnett test.

The following examples illustrate the invention without limiting the scope thereof.

EXAMPLE 1

Figure 1:
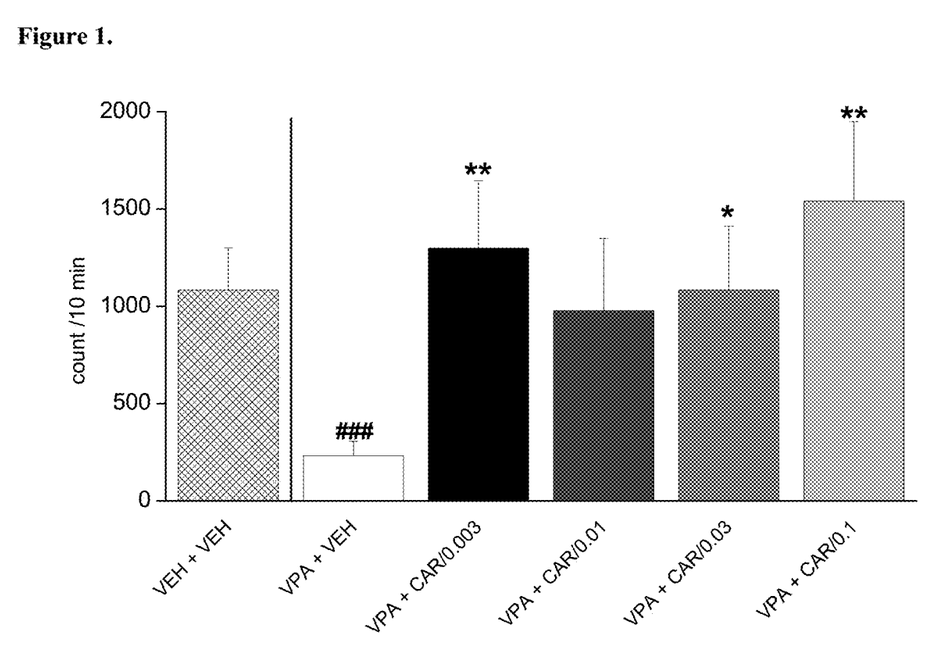
FIG. 1. Acute per os administration of trans-N-[4-[2-[4-(2,3-dichlorophenyl)piperazin-1-yl]ethyl]cyclohexyl]-N',N'-dimethylurea hydrochloride (cariprazine) reversed the socio-communicational deficit induced by prenatal valproate treatment (### $p<0.001$; Dunnett multiple comparisons test versus "VPA+VEH"). The effect of cariprazine was statistically significant at the doses of 0.003, 0.03 and 0.1 mg/kg (*, **$p<0.05$, $<0.01$; Dunnett test versus "VPA+VEH"). VEH +VEH means prenatal vehicle treatment combined with vehicle treatment before behavioral testing. VPA+VEH animals received prenatal VPA combined with vehicle treatment before behavioral testing. VPA+CAR/0.003, CAR/0.01, CAR/0.03 and CAR/0.1 groups received prenatal VPA followed by 0.003, 0.01, 0.03 and 0.1 mg/kg cariprazine, respectively.

Trans-N-[4[2-[4-(2,3-dichlorophenyl)piperazin-1-yl]ethyl]cyclohexyl]-N', N'-dimethylurea hydrochloride (cariprazine) was tested on rat pup communication in prenatally valproate-treated rats. Rat pup ultrasonic vocalization (USV) was evoked by maternal deprivation. The effect of acute administration of cariprazine on rat pup communication is shown in FIG. 1. The data represented are mean number of USV vocalizations±SEM of 13-24 rat pups for each group (both male and female pups were included). Cariprazine given orally increased and fully reversed isolation-induced vocalizations in valproate-treated offspring at the doses of 0.003, 0.03 and 0.1 mg/kg. Thus, cariprazine was able to reduce the socio-communicational deficit induced by prenatal valproate treatment.

EXAMPLE 2

Figure 2:
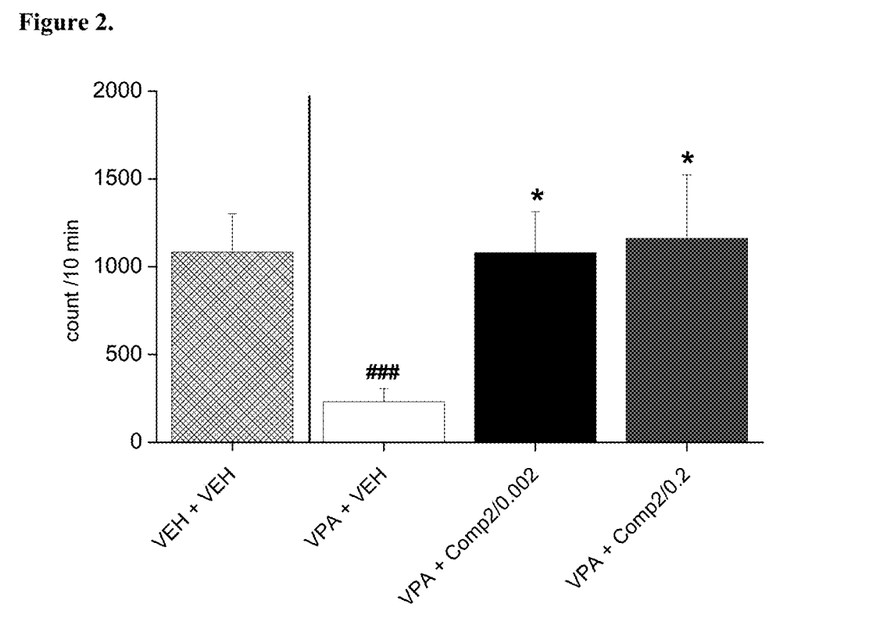
FIG. 2. Acute per os administration of trans-N-(4-{2-[4-(2,3-dichloro-phenyl)-piperazine-1-yl]-ethyl}-cyclohexyl)-morpholine-4 carboxamide hydrochloride (Compound 2) reversed the socio-communicational deficit induced by prenatal valproate treatment (### $p<0.001$; Dunnett multiple comparisons test versus "VPA+VEH"). The effect of Compound 2 was statistically significant at both investigated doses (*$p<0.05$; Dunnett test versus "VPA+VEH"). VEH+VEH means prenatal vehicle treatment combined with vehicle treatment before behavioral testing. VPA+VEH animals received prenatal VPA combined with vehicle treatment before behavioral testing. VPA+Comp2/0.002, and Comp2/0.2 groups received prenatal VPA followed by 0.002 and 0.2 mg/kg Compound2, respectively.

Trans-N-(4-{2-[4-(2,3-dichloro-phenyl)-piperazine-1-yl]ethyl}-cyclohexyl)-morpholine-4 carboxamide hydrochloride (Compound 2) was tested on rat pup communication in prenatally valproate-treated rats. Rat pup ultrasonic vocalization (USV) was evoked by maternal deprivation. The effect of acute oral administration of Compound 2 on rat pup communication is shown in FIG. 2. The data represented are mean number of USV vocalizations±SEM of 13-24 rat pups for each group (both male and female pups were included). Compound 2 given orally increased and fully reversed isolation-induced vocalizations in valproate-treated offspring at each dose examined. Thus, Compound 2 was able to reduce the socio-communicational deficit induced by prenatal valproate treatment.

EXAMPLE 3

Figure 3:
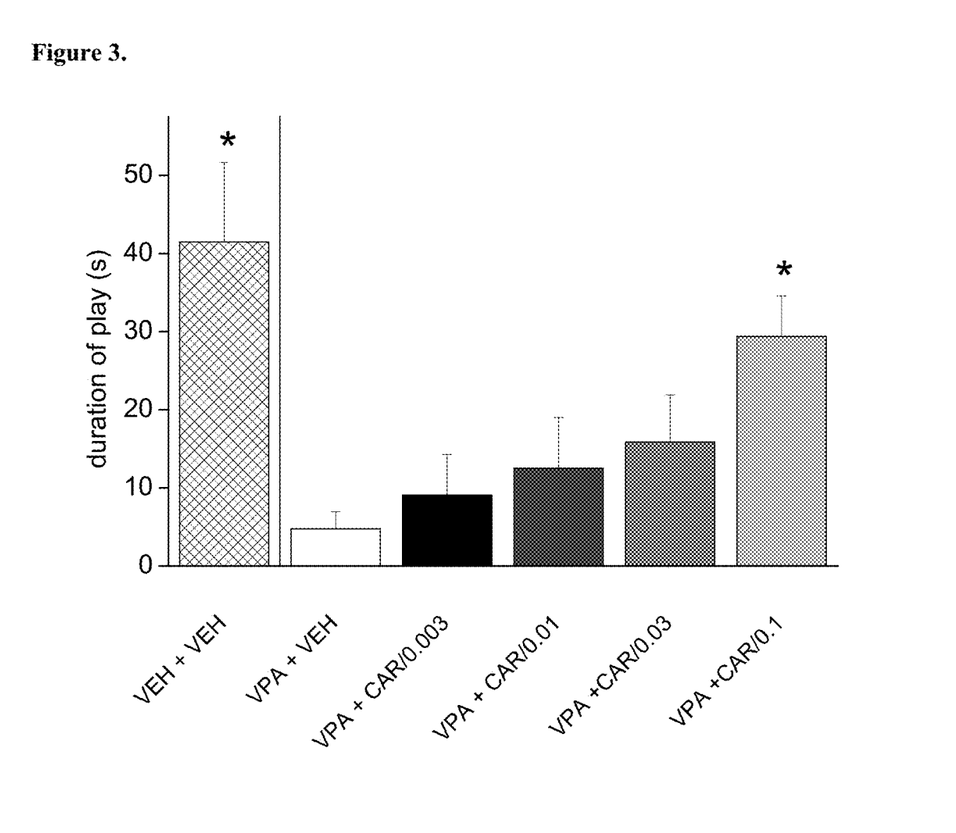
FIG. 3. Repeated (daily treatments for 8 days) per os administration of trans-N-[4-[2-[4-(2,3-dichlorophenyl)piperazin-1-yl]ethyl]cyclohexyl]- N',N'-dimethylurea hydrochloride (cariprazine) reversed the social play deficit induced by prenatal valproate treatment. The effect of cariprazine was statistically significant at the dose of 0.1 mg/kg (*$p<0.05$; Dunnett test versus "VPA+VEH"). VEH+VEH means prenatal vehicle treatment combined with vehicle treatment before behavioral testing. VPA+VEH animals received prenatal VPA combined with vehicle treatment before behavioral testing. VPA+CAR/0.003, CAR/0.01, CAR/0.03 and CAR/0.1 groups received prenatal VPA followed by 0.003, 0.01, 0.03 and 0.1 mg/kg cariprazine, respectively.

Trans-N-[4-[2-[4-(2,3-dichlorophenyl)piperazin-1-yl]ethyl]cyclohexyl]-N',N'-dimethylurea hydrochloride (cariprazine) was tested on rat social play behavior in prenatally valproate-treated rats. The effect of repeated dosing of cariprazine is shown in FIG. 3. The data presented are mean time spent playing±SEM of 4 pairs of rats for each group (only male offspring tested). Cariprazine administered orally increased and partially nevertheless, significantly reversed the social play deficit induced by prenatal valproate treatment. Therefore, cariprazine was able to reduce the socio-communicational deficit induced by prenatal valproate treatment.

EXAMPLE 4

Figure 4:
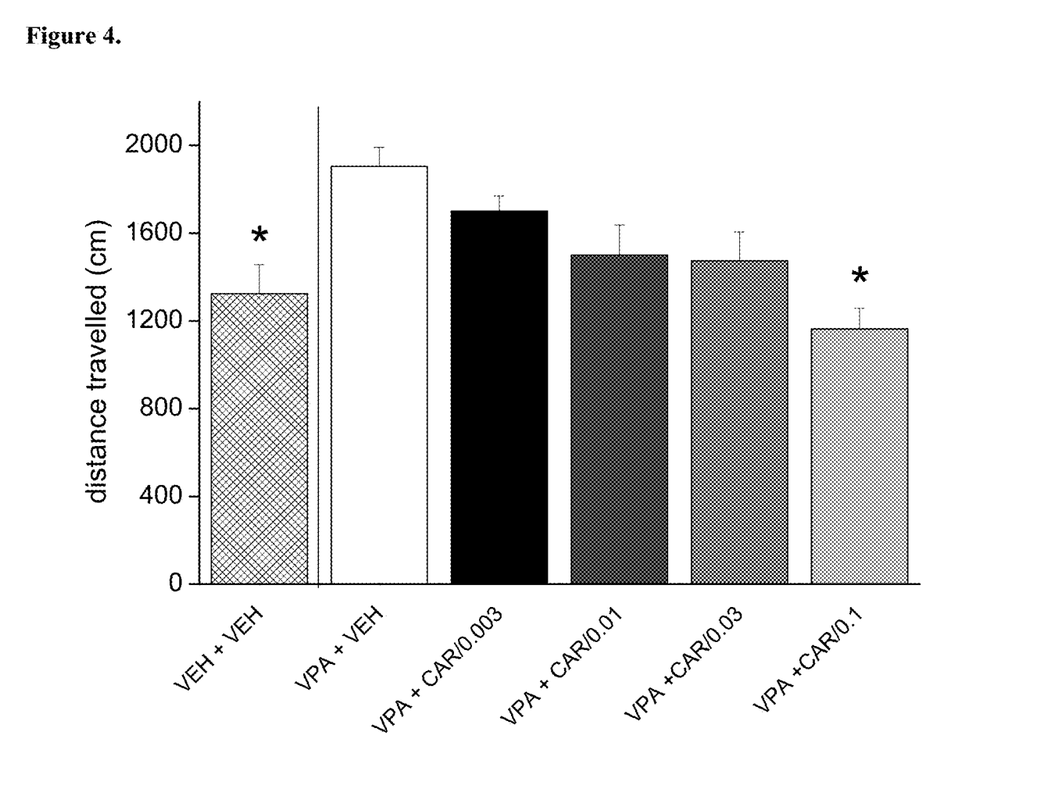
FIG. 4. Repeated (daily treatments for 9 days) per os administration of trans-N-[4-[2-[4-(2,3-dichlorophenyl)piperazin-1-yl]ethyl]cyclohexyl]- N',N'-dimethylurea hydrochloride (cariprazine) reversed the hyperactivity induced by prenatal valproate treatment. The effect of cariprazine was statistically significant at the dose of 0.1 mg/kg (*p<0.05; Dunnett test versus "VPA+VEH"). VEH+VEH means prenatal vehicle treatment combined with vehicle treatment before behavioral testing. VPA+VEH animals received prenatal VPA combined with vehicle treatment before behavioral testing. VPA+CAR/0.003, CAR/0.01, CAR/0.03 and CAR/0.1 groups received prenatal VPA followed by 0.003, 0.01, 0.03 and 0.1 mg/kg cariprazine, respectively.

Trans-N-[4-[2-[4-(2,3-dichlorophenyl)piperazin-1-yl]ethyl]cyclohexyl]-N',N'-dimethylurea hydrochloride (cariprazine) was tested on rat motility in the open field assay in prenatally valproate-treated rats. The effect of repeated dosing of cariprazine is shown in FIG. 4. The data presented are mean distance travelled±SEM of 8 rats for each group (only male offspring tested). Cariprazine administered orally reduced and fully reversed the excessive motility induced by prenatal valproate treatment. Therefore, cariprazine was able to reduce the hyperactivity induced by prenatal valproate treatment.

EXAMPLE 5

Figure 5:
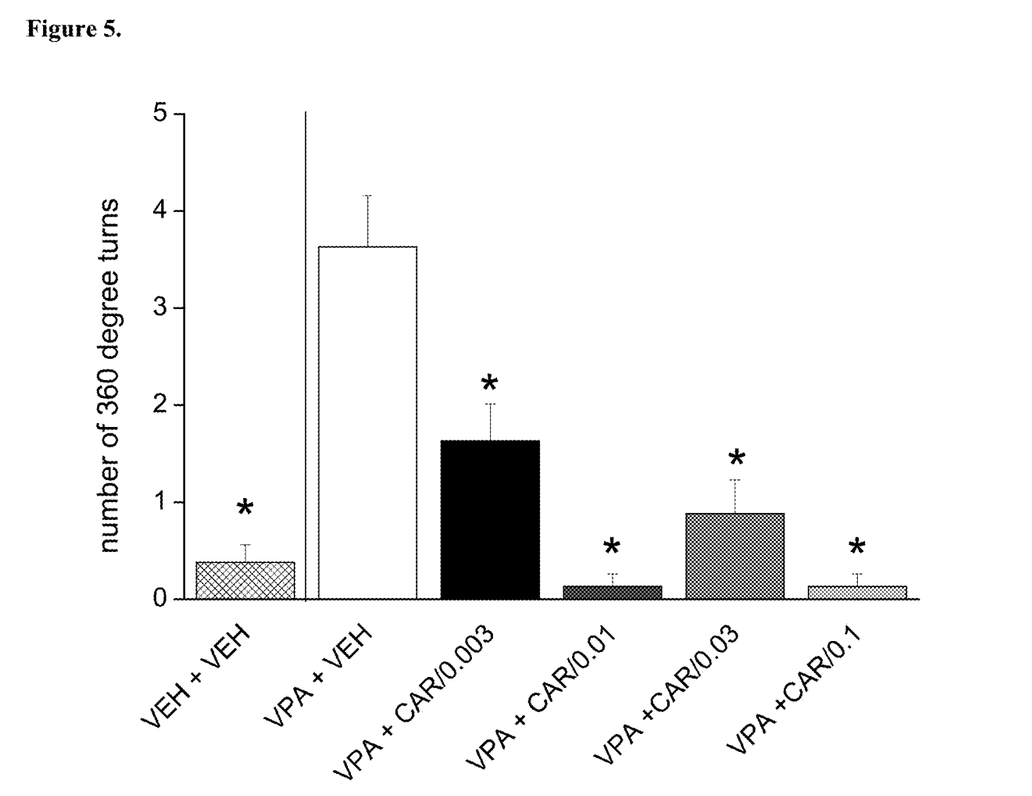
FIG. 5. Repeated (daily treatments for 9 days) per os administration of trans-N-[4-[2-[4-(2,3-dichlorophenyl)piperazin-1-yl]ethyl]cyclohexyl]- N',N'-dimethylurea hydrochloride (cariprazine) reversed the excessive circling behavior induced by prenatal valproate treatment. The effect of cariprazine was statistically significant at all doses of cariprazine (*p<0.05; Dunnett test versus "VPA+VEH"). VEH+VEH means prenatal vehicle treatment combined with vehicle treatment before behavioral testing. VPA+VEH animals received prenatal VPA combined with vehicle treatment before behavioral testing. VPA+CAR/0.003, CAR/0.01, CAR/0.03 and CAR/0.1 groups received prenatal VPA followed by 0.003, 0.01, 0.03 and 0.1 mg/kg cariprazine, respectively.

Trans-N-[4-[2-[4-(2,3-dichlorophenyl)piperazin-1-yl]ethyl]cyclohexyl]-N', N'-dimethyl urea hydrochloride (cariprazine) was tested on rat stereotypic behavior in the open field assay in prenatally valproate-treated rats. The effect of repeated dosing of cariprazine is shown in FIG. 5. The data presented are mean number of 360-degree turns±SEM of 8 rats for each group (only male offspring tested). Cariprazine administered orally reduced and fully reversed the excessive circling behavior induced by prenatal valproate treatment. Therefore, cariprazine was able to reduce the stereotypic behavior induced by prenatal valproate treatment.

EXAMPLE 6

Figure 6:
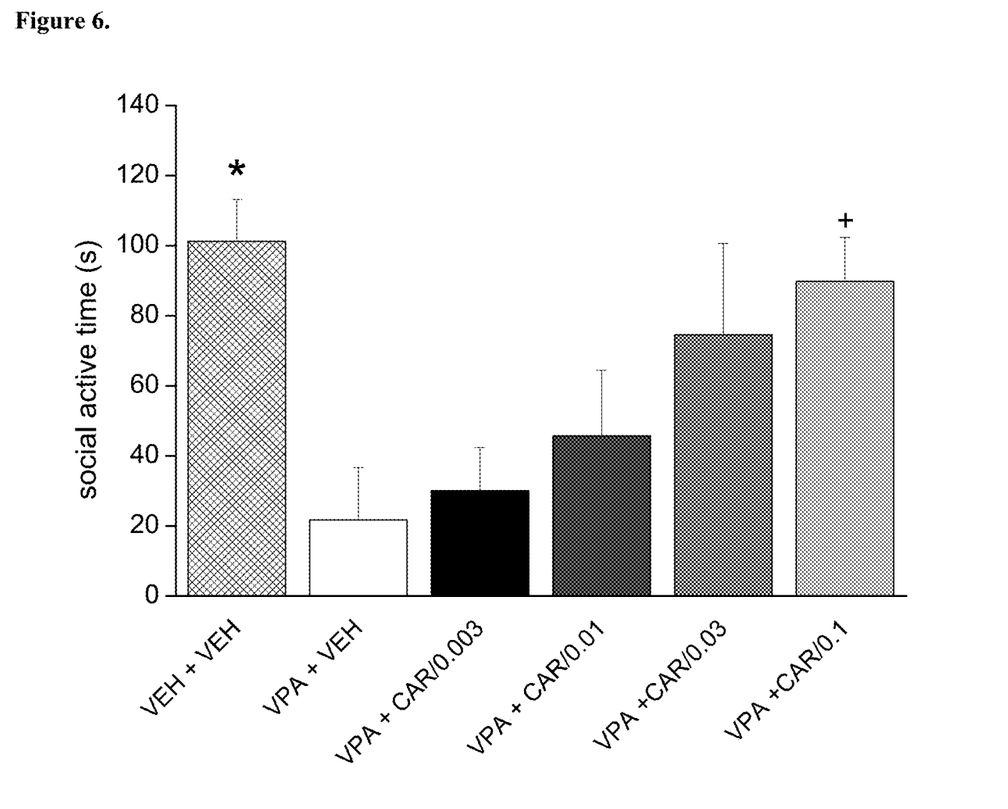
FIG. 6. Repeated (daily treatments for 8 days) per os administration of trans-N-[4-[2-[4-(2,3-dichlorophenyl)piperazin-1-yl]ethyl]cyclohexyl]- N',N'-dimethylurea hydrochloride (cariprazine) reversed the social preference deficit induced by prenatal valproate treatment. The effect of cariprazine was statistically significant at the dose of 0.1 mg/kg (*p<0.05; Dunnett test versus "VPA+VEH"). VEH+VEH means prenatal vehicle treatment combined with vehicle treatment before behavioral testing. VPA+VEH animals received prenatal VPA combined with vehicle treatment before behavioral testing. VPA+CAR/0.003, CAR/0.01, CAR/0.03 and CAR/0.1 groups received prenatal VPA followed by 0.003, 0.01, 0.03 and 0.1 mg/kg cariprazine, respectively.

Trans-N-[4-[2-[4-(2,3-dichlorophenyl)piperazin-1-yl]ethyl]cyclohexyl]-N', N'-dimethyl urea hydrochloride (cariprazine) was tested on rat social preference behavior in the 3-chamber assay in prenatally valproate-treated rats. The effect of repeated dosing of cariprazine is shown in FIG. 6. The data presented are mean duration of social investigation±SEM of 8 rats for each group (only male offspring tested). Cariprazine administered orally increased and nearly fully reversed the social deficit induced by prenatal valproate treatment. Therefore, cariprazine was able to reduce the socio-communicational deficit induced by prenatal valproate treatment.

The invention claimed is:

1. A method of treating one or more symptoms of autism spectrum disorder in a subject, comprising administering trans-N-[4-[2-[4-(2,3-dichlorophenyl)piperazin-1-yl]ethyl]cyclohexyl]-N',N'-dimethylurea and/or pharmaceutically acceptable salts thereof to the subject.

2. The method according to claim 1 wherein the one or more symptoms of autism spectrum disorder comprise socio-communicational deficits.

3. The method according to claim 1, wherein the one or more symptoms of autism spectrum disorder comprise restricted and repetitive behaviors.

4. The method according to claim 1, wherein the one or more symptoms of autism spectrum disorder comprise irritability.

5. The method according to claim 1, wherein the one or more symptoms of autism spectrum disorder comprise attention deficit and hyperactivity.

6. The method according to claim 1, wherein trans-N-[4-[2-[4-(2,3-dichlorophenyl)piperazin-1-yl]ethyl]cyclohexyl]-N',N'-dimethylurea is in the form of trans-N-[4-[2-[4-(2,3-dichlorophenyl)piperazin-1-yl]ethyl]cyclohexyl]-N',N'dimethylurea hydrochloride.

7. The method of claim 1, wherein the transN-[4-[2-[4-(2,3-dichlorophenyl)piperazin-1-yl]ethyl]cyclohexyl]-N',N'-dimethylurea is further formulated as a pharmaceutical composition comprising transN-[4-[2-[4-(2,3-dichlorophenyl)piperazin-1-yl]ethyl]cyclohexyl]-N',N'-dimethylurea and/or pharmaceutically acceptable salts thereof and a pharmaceutically acceptable excipient.

8. The method of claim 1, wherein the transN-[4-[2-[4-(2,3-dichlorophenyl)piperazin-1-yl]ethyl]cyclohexyl]-N',N'-dimethylurea close and/or pharmaceutically acceptable salts thereof is further administered in combination with at least one adjunctive therapeutic agent.

9. The method according to claim 8, wherein the at least one adjunctive therapeutic agent is selected from the group consisting of psychostimulants/nootropics, antipsychotics, antidepressants, anxiolytics, antihypertensives, antiepileptics, narcotics and spasmolytics.

10. A method for treating a disease or disorder selected from Asperger's syndrome, atypical autism, Rett syndrome, childhood disintegrative disorder, and sensory integration dysfunction, comprising administering to a patient in need thereof a pharmaceutically effective amount of trans-N-[4-[2-[4-(2,3-dichlorophenyl)piperazin-1-yl]ethyl]cyclohexyl]-N',N'-dimethylurea or a pharmaceutically acceptable salt thereof.

11. The method according to claim 10 wherein said disease or disorder is Asperger's syndrome.

12. The method according to claim 10 wherein said disease or disorder is atypical autism.

13. The method according to claim 10 wherein said disease or disorder is Rett syndrome.

14. The method according to claim 10 wherein said disease or disorder is childhood disintegrative disorder.

15. The method according to claim 10 wherein said disease or disorder is sensory integration dysfunction.

* * * * *

UNITED STATES PATENT AND TRADEMARK OFFICE
CERTIFICATE OF CORRECTION

PATENT NO. : 11,547,707 B2
APPLICATION NO. : 16/845192
DATED : January 10, 2023
INVENTOR(S) : Viktor Román et al.

It is certified that error appears in the above-identified patent and that said Letters Patent is hereby corrected as shown below:

In the Claims

Column 15, Line 26, in Claim 7, delete ",N'dimethylurea" and insert -- ,N'-dimethylurea --.

Column 15, Line 27, in Claim 7, delete "transN" and insert -- trans-N --.

Column 15, Line 30, in Claim 7, delete "transN" and insert -- trans-N --.

Column 16, Line 3, in Claim 8, delete "transN" and insert -- trans-N --.

Column 16, Line 5, in Claim 8, after "dimethylurea" delete "close".

Signed and Sealed this
Twenty-eighth Day of March, 2023

Katherine Kelly Vidal
*Director of the United States Patent and Trademark Office*